United States Patent
Ames

(10) Patent No.: US 8,585,403 B2
(45) Date of Patent: Nov. 19, 2013

(54) DENTAL APPLIANCE AND METHOD FOR REMOVING BODILY AND OTHER FLUIDS FROM A DENTAL SITE

(71) Applicant: Inger-Marie Ames, Port St. Lucie, FL (US)

(72) Inventor: Inger-Marie Ames, Port St. Lucie, FL (US)

( * ) Notice: Subject to any disclaimer, the term of this patent is extended or adjusted under 35 U.S.C. 154(b) by 0 days.

(21) Appl. No.: 13/648,440

(22) Filed: Oct. 10, 2012

(65) Prior Publication Data

US 2013/0095450 A1 Apr. 18, 2013

Related U.S. Application Data

(60) Provisional application No. 61/547,084, filed on Oct. 14, 2011.

(51) Int. Cl.
*A61C 17/06* (2006.01)
*A61C 17/10* (2006.01)

(52) U.S. Cl.
USPC ............... 433/93; 433/96; 433/215; 604/902

(58) Field of Classification Search
USPC .............. 433/91–96, 140, 215; 600/237–244, 600/203; 604/540, 541, 543, 902, 313, 314, 604/316, 96.01, 164.01, 523, 315, 48, 131, 604/542, 544; 239/548, 567; 4/618
See application file for complete search history.

(56) References Cited

U.S. PATENT DOCUMENTS

| | | | | |
|---|---|---|---|---|
| 683,076 A | * | 9/1901 | Simmons | 4/618 |
| 759,874 A | * | 5/1904 | Fletcher | 4/618 |
| 950,269 A | * | 2/1910 | Youngs | 4/567 |
| 951,130 A | * | 3/1910 | Jordan | 433/93 |
| 1,012,613 A | * | 12/1911 | Witt | 433/91 |
| 1,202,264 A | * | 10/1916 | Brown | 433/93 |
| 1,374,430 A | * | 4/1921 | Chevalier | 4/618 |
| 1,401,646 A | * | 12/1921 | Ronn | 433/93 |
| 1,501,010 A | * | 7/1924 | Dailey | 433/91 |
| 1,891,690 A | * | 12/1932 | Rickey | 2/240 |
| 1,930,196 A | * | 10/1933 | Fisher | 433/94 |
| 2,286,462 A | * | 6/1942 | Chaffin | 604/43 |
| 2,483,851 A | * | 10/1949 | Smith | 604/195 |
| 2,492,384 A | * | 12/1949 | Kaslow | 604/43 |

(Continued)

FOREIGN PATENT DOCUMENTS

| | | | |
|---|---|---|---|
| EP | 0003470 A2 | * | 8/1979 |
| WO | WO 9316741 A1 | * | 9/1993 |
| WO | WO 02/083025 A1 | * | 10/2002 |

*Primary Examiner* — Robyn Doan
*Assistant Examiner* — Michael R Ballinger
(74) *Attorney, Agent, or Firm* — Edell, Shapiro & Finnan, LLC

(57) ABSTRACT

According to a present invention embodiment, a dental appliance maintains a patient mouth in an open state, retracts tissue, and evacuates bodily and/or other fluids from a dental site. The dental appliance includes an elongated tube configured with a looped section. The elongated tube is flexible, where the looped section is adjustable and manipulated to enable the dental appliance to accommodate mouths of various dental patients. Further, the looped section is resilient in order to maintain the patient mouth in an open state for dental procedures. In addition, the elongated tube includes perforations to remove bodily or other fluids from the patient mouth. A vacuum or suction device is coupled to an end of the elongated tube, where suction is applied to the tube to draw bodily or other fluids from the patient mouth through the perforations and remove these fluids from a dental site.

19 Claims, 4 Drawing Sheets

(56) References Cited

U.S. PATENT DOCUMENTS

| | | | |
|---|---|---|---|
| 2,672,143 A * | 3/1954 | Gold et al. | 433/80 |
| 2,701,916 A * | 2/1955 | Jarboe | 433/96 |
| 2,873,528 A * | 2/1959 | Thompson | 433/93 |
| 3,049,806 A * | 8/1962 | Cofresi | 433/93 |
| 3,155,097 A * | 11/1964 | Barron | 604/265 |
| 3,376,868 A * | 4/1968 | Mondiadis | 604/133 |
| 3,461,863 A * | 8/1969 | Sullinger | 600/41 |
| 3,631,598 A * | 1/1972 | Lussier | 433/94 |
| 4,053,984 A | 10/1977 | Moss | |
| D258,531 S * | 3/1981 | Orsing | D24/112 |
| 4,325,695 A * | 4/1982 | Sundelin et al. | 433/91 |
| 4,417,874 A * | 11/1983 | Andersson et al. | 433/96 |
| 4,643,720 A * | 2/1987 | Lanciano | 604/95.04 |
| 5,211,639 A * | 5/1993 | Wilk | 604/317 |
| 5,322,521 A * | 6/1994 | Wilk | 604/317 |
| 5,873,718 A | 2/1999 | Sullivan | |
| 5,931,673 A * | 8/1999 | Bolbolan | 433/136 |
| 5,941,873 A * | 8/1999 | Korenfeld | 606/1 |
| 6,988,893 B2 | 1/2006 | Haywood | |
| 7,141,047 B2 * | 11/2006 | John | 604/541 |
| 8,464,709 B2 * | 6/2013 | Wedemeyer | 128/200.26 |
| 2004/0122352 A1* | 6/2004 | John | 604/35 |
| 2008/0091146 A1* | 4/2008 | Solovay et al. | 604/174 |
| 2012/0237894 A1* | 9/2012 | Maycher et al. | 433/95 |

* cited by examiner

DENTAL APPLIANCE AND METHOD FOR REMOVING BODILY AND OTHER FLUIDS FROM A DENTAL SITE

CROSS-REFERENCE TO RELATED APPLICATION

This application claims priority from U.S. Provisional Patent Application Ser. No. 61/547,084, entitled "Saliva Ejector" and filed Oct. 14, 2011, the disclosure of which is incorporated herein by reference in its entirety.

BACKGROUND

1. Technical Field

Present invention embodiments relate to dental appliances and, in particular, to devices for propping the mouth open, retracting tissue, and evacuating fluids from the mouth.

2. Discussion of Related Art

Dental practitioners and technicians remove saliva and water from a mouth, retract lips and cheeks, and prop the mouth open during dental procedures in order to provide a dry and unobstructed field of operation. Typically, separate devices are utilized to perform these functions.

In particular, saliva ejectors are employed to evacuate saliva from a dental site. Generally, the saliva ejectors comprise a plastic tube with a wire to provide stability, and have a single opening at a tip of the tube through which saliva is evacuated. The tube and wire must be bent to the desired shape to conform to a particular patient's mouth. During use, tissues become trapped in the opening, thereby obstructing suction and causing trauma to the soft tissues. Further, the saliva ejectors evacuate only one side of the mouth at a time, and impede visibility and access to dental sites.

Although cotton rolls may be placed in the oral vestibule for retraction, the cotton rolls become overly wet with saliva during the dental procedure. Moreover, retraction devices that are mostly used for photography may be placed at the corners of the lips. These devices retract only one area at a time, and must be held in place by a dental practitioner which can result in operator fatigue. Other retraction devices are bulky, cumbersome, obstruct visibility, and can be used on only one side of the mouth at a time.

Current devices to maintain the mouth in an open state consist of a rubber wedge, and are usually not disposable. These devices are bulky, restrict visibility, and allow access to only one side of the mouth at a time. A patient can neither voluntary close nor relax the jaw, and the lips cannot close over the device. In addition, the dimensions of the device prohibit placement in certain patients that are unable to sufficiently open their mouth.

BRIEF SUMMARY

According to an embodiment of the present invention, a dental appliance is used to maintain a patient mouth in an open state, retract tissue, and evacuate bodily and other fluids from a dental site. The dental appliance includes an elongated tube configured with a looped section. The elongated tube is flexible, where the looped section is adjustable and manipulated to enable the dental appliance to accommodate mouths of various dental patients. Further, the looped section is resilient in order to maintain the patient mouth in an open state for dental procedures. In addition, the elongated tube includes perforations to remove bodily or other fluids from the patient mouth. A vacuum or suction device is coupled to an end of the elongated tube, where suction is applied to the tube to draw bodily or other fluids from the patient mouth through the perforations and remove these fluids from a dental site.

One aspect of a present invention embodiment is to provide continuous bilateral suction unimpeded by the tongue, lips, and/or cheeks to evacuate bodily and/or other fluids from a patient mouth.

Another aspect of a present invention embodiment is to retract cheeks and lips of a dental patient to provide improved visibility and access for a dental practitioner during dental procedures.

Yet another aspect of a present invention embodiment is to relieve a dental patient of having to hold the jaw open, while allowing the dental patient to close the jaw.

Still another aspect of a present invention embodiment is to adjust a dental appliance to accommodate the mouth of various dental patients.

Further aspects of present invention embodiments include fitting the dental appliance in the oral vestibule to be away from working areas; reducing drag on the patient's lip through a lightweight appliance; reducing stress on the patient's temporomandibular joint; and providing a device that is disposable after a single use.

The aforesaid aspects may be achieved individually or in combination, and it is not intended that present invention embodiments be construed as requiring two or more of the aspects to be combined unless expressly required by the claims attached hereto.

The above and still further aspects, features, and advantages of the present invention will become apparent upon consideration of the following detailed description of example embodiments thereof, particularly when taken in conjunction with the accompanying drawings, wherein like reference numerals in the various figures designate like components.

DETAILED DESCRIPTION

Figure 1:
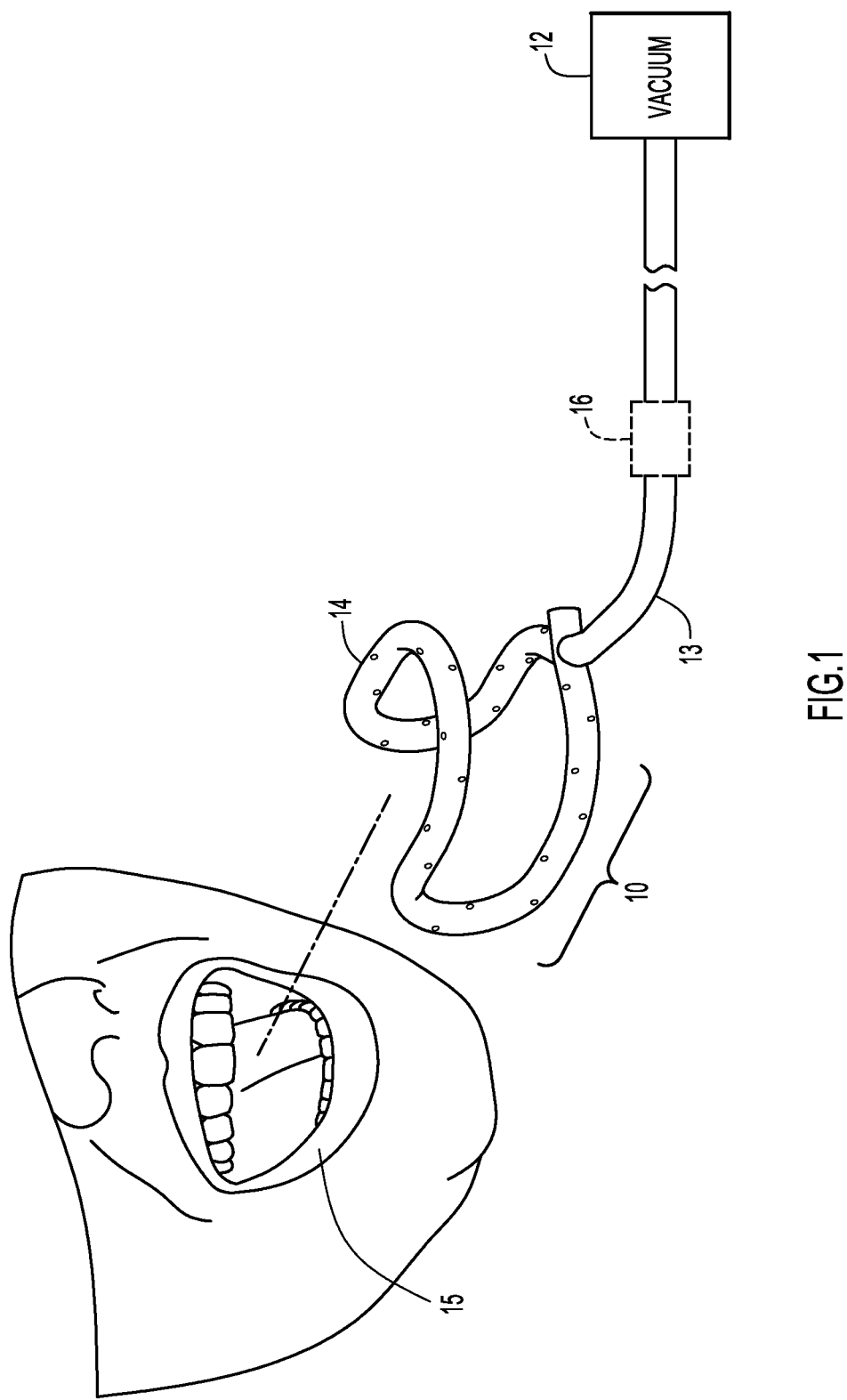
FIG. 1 is an exploded view in perspective of a dental appliance according to an embodiment of the present invention configured for placement within a patient mouth.

A dental appliance to remove bodily and/or other fluids (e.g., saliva, water, etc.), retract lips and/or cheeks, and maintain a patient mouth in an open state during dental procedures is illustrated in FIG. 1. Specifically, a dental appliance 10 includes a flexible looped section 14 that is manipulated to fit within a patient oral vestibule 15 (e.g., a region between the lips or cheeks and the teeth, maxilla, or mandible). The dental appliance further comprises a connector section 13 that is coupled to a vacuum or suction system 12 at interface 16. The vacuum system may be implemented by any suitable dental or other vacuum system, and applies suction to the dental appliance to remove bodily and/or other fluids from the patient mouth during dental procedures. Looped section 14 includes perforations to enable the bodily and/or other fluids to be drawn into the looped section via the suction provided by vacuum device 12. In addition, looped section 14 is resilient and further serves to maintain the patient mouth in an open state.

Figure 2:
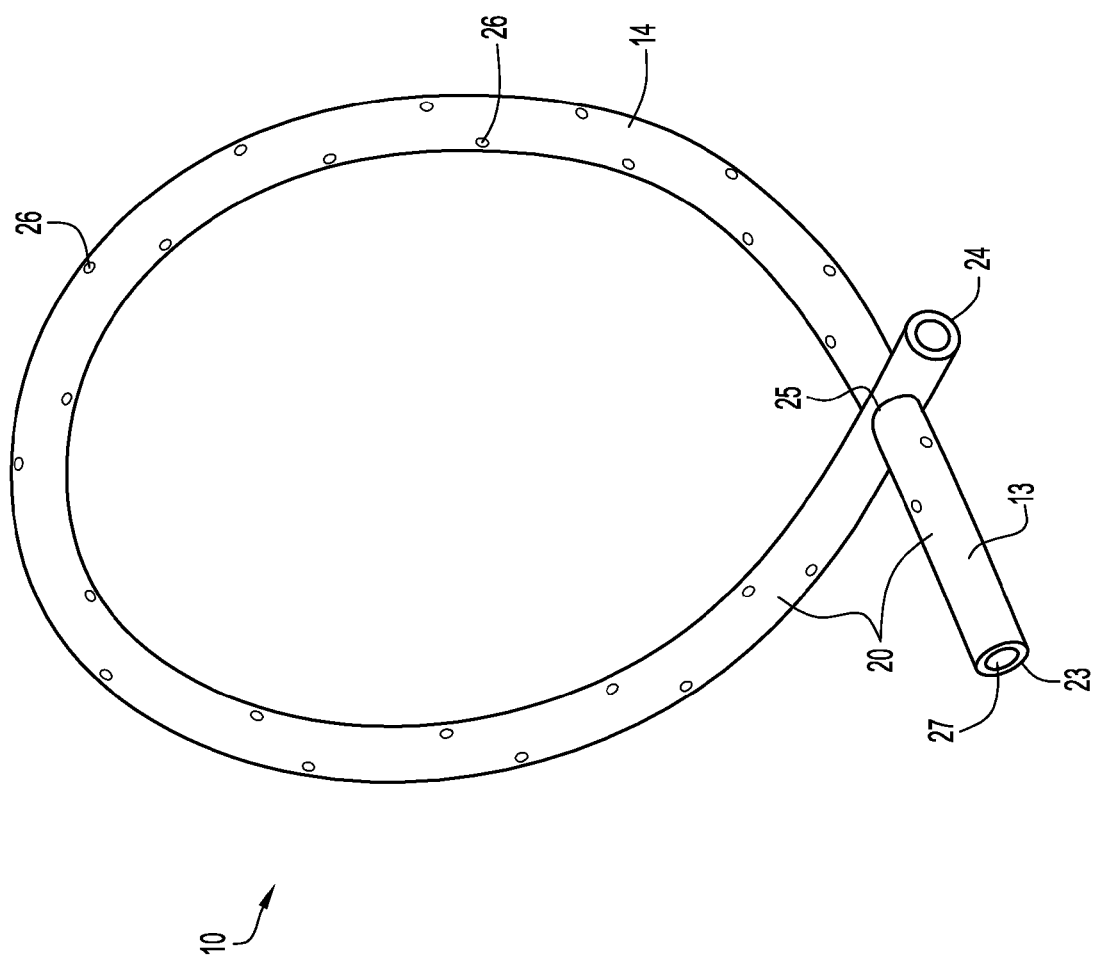
FIG. 2 is a view in perspective of a dental appliance according to an embodiment of the present invention.

Dental appliance 10 according to an embodiment of the present invention is illustrated in FIG. 2. Specifically, dental appliance 10 comprises an elongated tube 20 having a proximal end 23, a distal end 24, an intersecting junction 25, perforations 26, and a channel 27. Tube 20 is configured to form connector section 13 and looped section 14, and includes channel 27 extending therethrough to provide a path for bodily and/or other fluids to flow within the tube from a patient mouth. Connector section 13 includes tube proximal end 23 and extends therefrom to looped section 14. Proximal end 23 is preferably configured for a friction fit with vacuum system 12 to provide suction for the dental appliance, where the friction fit serves as interface 16. Alternatively, interface 16 includes an adaptor for coupling the connector section to vacuum system 12.

Looped section 14 interfaces connector section 13 at intersecting junction 25 disposed proximate tube distal end 24. Tube 20 extends from connector section 13 through intersecting junction 25, and is arranged to slidably engage itself at intersecting junction 25 as described below to form looped section 14. Tube 20 comprises a soft plastic texturing on a tube outer surface to contact interior surfaces of a patient mouth. Tube 20 is disposable and constructed of materials with sufficient resilience to maintain a patient mouth or jaw in an open state, while allowing the patient to close the mouth or jaw. The tube is preferably substantially cylindrical, and includes dimensions sufficient to fit comfortably within a patient mouth behind the lips and provide desired retraction of the lips and cheeks. By way of example, tube 20 has an outer diameter of approximately 0.25 inches, an inner diameter of approximately 0.125 inches, and a length of approximately fourteen inches. However, the tube may include any desired shape (e.g., oval, square/rectangular, etc.), and have any suitable dimensions.

Perforations 26 are defined in connector section 13 and looped section 14 of tube 20 to enable removal of bodily and/or other fluids from a patient mouth. The perforations are in the form of generally circular apertures or openings and are defined along connector section 13 and looped section 14 of tube 20. The perforations may be defined at any suitable locations on the surface of the tube (e.g., along the circumference or perimeter of the tube), and, by way of example, may be distributed in a random fashion. This prevents contact between a portion of the tube and oral tissues (e.g., the cheeks and lips) from obstructing evacuation of bodily and/or other fluids from the patient mouth. The perforations may alternatively be distributed in any desired pattern (e.g., linear, spiral, curved or non-linear, etc.).

Perforations 26 include dimensions sufficient to avoid trapping and traumatizing soft mouth tissue, while enabling bodily and/or other fluids (e.g., saliva, water, etc.) to be drawn therethrough into dental appliance 10. By way of example, perforations 26 have diameters between ten and forty mil, and pairs of perforations are longitudinally disposed at approximately half inch intervals, where the perforations of each pair are angularly spaced apart by approximately one-hundred eighty degrees. However, the perforations may be of any quantity or shape, may be disposed at any suitable locations, and may include any suitable dimensions.

Figure 3:
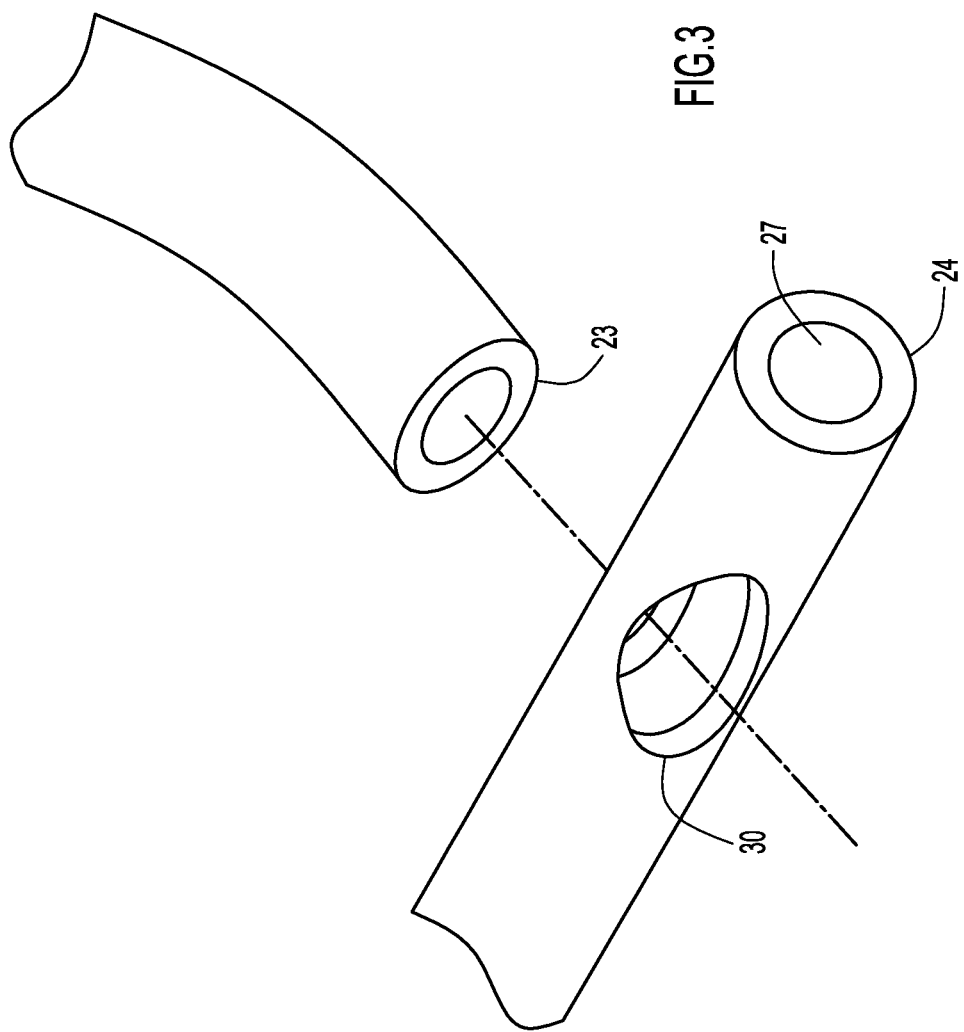
FIG. 3 is an exploded view in perspective of an intersecting junction of a dental appliance according to an embodiment of the present invention.

Referring to FIG. 3, intersecting junction 25 is disposed proximate tube distal end 24 and enables tube 20 to slidably engage itself to form looped section 14. Intersecting junction 25 comprises generally circular apertures 30 that are defined in tube 20 substantially coincident each other and angularly spaced by approximately one-hundred eighty degrees. The apertures basically provide a transverse path through tube 20 to enable slidable engagement with itself. The diameter of apertures 30 may be slightly less than or substantially the same as the outer diameter of tube 20 to enable the tube to traverse the transverse path formed by the apertures for a friction type fit. In particular, tube distal end 23 is inserted through apertures 30 to enable the tube to slidably engage itself and form a looped configuration for looped section 14. The tube may compress to fit through apertures 30 and provide a snug fit. The portion of tube 20 within intersecting junction 25 (or traversing apertures 30) effectively blocks channel 27 within the tube, thereby maintaining suction within the channel and enabling bodily and/or other fluids to be drawn through perforations 26. Friction generally maintains the position of tube 20 within apertures 30, while a dental practitioner may overcome the frictional forces to adjust the dimension of looped section 14 to accommodate the mouth of various patients. For example, sliding tube 20 through intersecting junction 25 to move the intersecting junction to a position closer to tube proximal end 23 enlarges the size of looped section 14, while sliding the tube through the intersecting junction to move the intersecting junction away from the tube proximal end reduces the size of the looped section. Thus, dental appliance 10 is adjustable to accommodate various patients.

Figure 4:
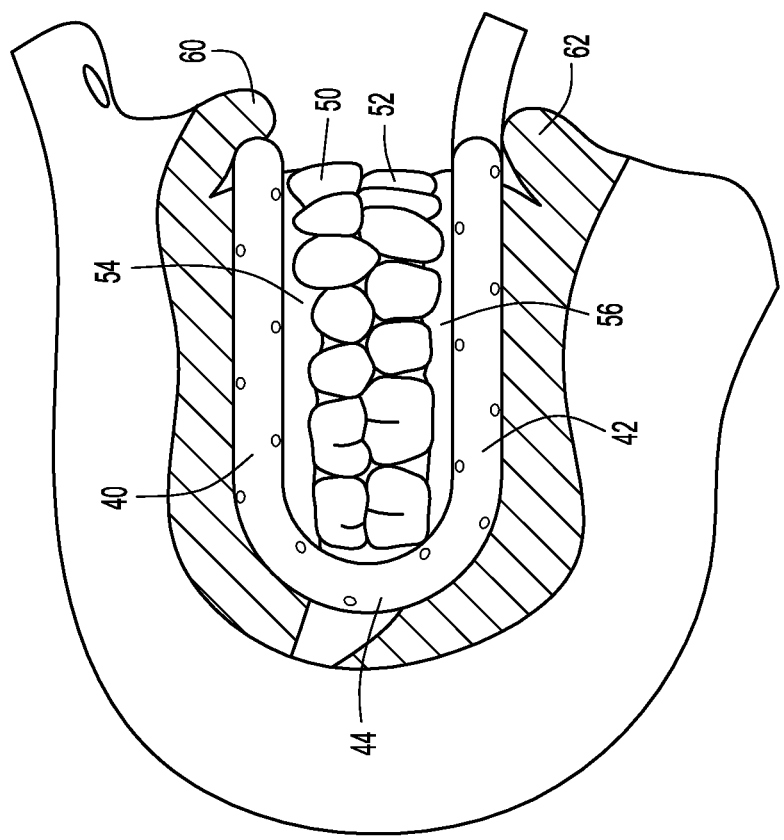
FIG. 4 is a view in elevation and partial section of a dental appliance disposed within a patient mouth according to an embodiment of the present invention.

A manner of operating dental appliance 10 to remove bodily and/or other fluids from a patient mouth is illustrated in FIGS. 1 and 4. Initially, a dental practitioner or other operator of dental appliance 10 adjusts looped section 14 to a desired size for a patient mouth (e.g., by sliding tube 20 through intersecting junction 25 as described above). The operator manipulates looped section 14 by basically bending the looped section over itself to have a configuration with a generally U-shaped upper portion 40, a generally U-shaped lower portion 42, and generally C-shaped rear portions 44 connecting respective sides of the upper and lower portions. The upper and lower portions are substantially coincident each other, where the resulting configuration of dental appliance 10 conforms to a curvature of a patient mouth. The dental appliance is inserted into a patient mouth with upper portion 40 disposed between upper lip 60 and/or cheeks (not shown) and maxilla 54 above upper teeth 50. Lower portion 42 is disposed between lower lip 62 and/or cheeks (not shown) and mandible 56 below lower teeth 52. The dental appliance retracts tissue and biases the patient mouth to an open state, where the patient may overcome the bias and close the mouth.

Connector section 13 preferably extends from lower portion 42 and is coupled to vacuum or suction system 12. The vacuum system may be coupled to tube proximal end 23 via a friction fit arrangement. Alternatively, connector section 13 may include an adaptor for coupling to the vacuum system. The vacuum system provides suction through channel 27 of tube 20 to draw bodily and/or other fluids within the patient mouth through perforations 26 and into looped section 14. The fluids traverse channel 27 to the vacuum system for disposal.

It will be appreciated that the embodiments described above and illustrated in the drawings represent only a few of the many ways of implementing a dental appliance and method for removing bodily and other fluids from a dental site.

The dental appliance may be of any shape or size, and preferably capable of being placed within a mouth. The dental appliance may couple to any conventional or other vacuum or suction system in any desired fashion (e.g., with or without an adaptor, with or without a conventional saliva ejector, using a friction connection, clip, adhesive, etc.). The connector and looped sections may be integral or non-integral (e.g., attached to each other via a T-connection or other connector or fastener).

The tube may be of any quantity, shape or size, and may be constructed of any suitable materials (e.g., any flexible, resilient tubing, medical tubing, food-grade tubing, etc.). The tube may intersect itself or remain disjoint and be connected by any suitable fastener (e.g., the looped section may be formed, and the size adjusted, using a C-clamp, figure-8-clamp, plastic tie, etc. to bind sections of tubing together). In the latter case, the distal end of the tube may be blocked to maintain suction at the perforations. Alternatively, the tube distal end may couple to the connector section (e.g., by insertion through a single aperture).

The perforations may be disposed in any pattern (e.g., random, periodic, spiral, etc.) in any groups (e.g., on sections of the tube surface, in pairs of azimuthally opposed perforations, etc.). The perforations may be of any quantity, shape or size, and may be disposed at any suitable locations on the tube. The apertures may be of any quantity, shape or size, and may be disposed at any suitable locations. The apertures may be larger or smaller than the outer diameter of the tubing to regulate the amount force required to adjust the size of the looped section. Any fastening or other mechanism may be used to prevent undesired sliding (e.g., a clamp, tie, etc.).

It is to be understood that the terms "front", "rear", "side", "top", "bottom", "upper", "lower", "upward", "downward", length", width, "horizontal", "vertical", "proximal", "distal" and the like are used herein merely to describe points of reference and do not limit the present invention to any particular configuration or orientation.

The present invention is not limited to the applications disclosed herein, but may be used with any type of evacuation or other system to evacuate any type of fluid from any desired site.

From the foregoing description, it will be appreciated that the invention makes available a novel dental appliance and method for removing bodily and other fluids from a dental site, wherein the dental appliance includes a looped section with perforations for removing bodily and/or other fluids from a dental site.

Having described preferred embodiments of a new and improved dental appliance and method for removing bodily and other fluids from a dental site, it is believed that other modifications, variations, and changes will be suggested to those skilled in the art in view of the teaching set forth herein. It is therefore to be understood that all such variations, modifications, and changes are believed to fall within the scope of the present invention as defined by the appended claims.

What is claimed is:

1. A device to remove fluid from a dental site comprising:
an elongated tube including:
open proximal and distal ends with a channel defined within said elongated tube and extending between said open proximal and distal ends;
a looped section with openings defined therein to draw said fluid from said dental site into said channel via suction from a suction system, wherein a distal portion of said tube includes a plurality of apertures defined therein and a proximal portion of said tube is disposed through said apertures and blocks said channel to form said looped section, and wherein said proximal portion is slidably disposed through said apertures to adjust said looped section to accommodate various dental sites; and a connector section formed by said proximal portion of said tube extending beyond said plurality of apertures of said distal portion to couple said looped section to said suction system.

2. The device of claim 1, wherein said looped section includes a resilience sufficient to bias a jaw of a dental patient to an open state.

3. The device of claim 2, wherein said resilience is capable of being overcome by said dental patient to close said jaw.

4. The device of claim 1, wherein said openings are defined in said looped section in a pattern.

5. The device of claim 1, wherein said openings comprise uniformly spaced openings along said looped section of said tube.

6. The device of claim 5, wherein said uniformly spaced openings along said tube are spaced azimuthally to form a spiral pattern.

7. The device of claim 1, wherein said openings have a diameter between ten and forty mils.

8. A method of removing fluid from a dental site via a device including an elongated tube with open proximal and distal ends, with a channel defined within said elongated tube and extending between said open proximal and distal ends, and a connector section and a looped section comprising:
(a) manipulating said looped section to conform to a curvature of a patient mouth, wherein said looped section includes openings defined therein, wherein a distal portion of said tube includes a plurality of apertures defined therein and a proximal portion of said tube is disposed through said apertures and blocks said channel to form said looped section, and wherein said proximal portion is slidably disposed through said apertures to adjust said looped section to accommodate various dental sites, wherein said connector section is formed by said proximal portion of said tube extending beyond said plurality of apertures of said distal portion to couple said looped section to a suction system, and;
(b) placing said manipulated looped section into said patient mouth; and
(c) drawing said fluid from said patient mouth through said openings and into said channel of said looped section via suction from said suction system to remove said fluid from said dental site.

9. The method of claim 8, wherein said looped section has a size and is adjustable, and step (a) further includes:
(a.1) adjusting said size of said looped section to accommodate said patient mouth.

10. The method of claim 8, wherein step (b) further includes:
(b.1) retracting oral tissue to enable visibility of said dental site.

11. The method of claim 8, wherein step (b) further includes:
(b.1) biasing said patient mouth in an open state via resilience of said looped section.

12. The method of claim 11, wherein step (b) further includes:
(b.2) flexing said looped section in response to overcoming said bias to enable said jaw to close.

13. The method of claim 8, wherein said openings are defined in said looped section in a pattern.

14. The method of claim 8, wherein step (a) further includes:
(a.1) coupling said connector section to a suction system.

15. The method of claim 8, wherein step (b) further includes:

(b.3) placing a portion of said manipulated looped section within upper and lower labial vestibules of said patient mouth.

16. The method of claim 15, wherein step (b.1) further includes:

(b.3.1) retracting lips to enable visibility of said dental site.

17. The method of claim 8, wherein said openings comprise uniformly spaced openings along said looped section of said tube.

18. The method of claim 17, wherein said uniformly spaced openings along said tube are spaced azimuthally to form a spiral pattern.

19. The method of claim 8, wherein said openings have a diameter between ten and forty mils.

* * * * *